United States Patent [19]

Kawabata et al.

[11] 4,283,563
[45] Aug. 11, 1981

[54] PROCESS FOR PREPARATION OF ALDEHYDES

[75] Inventors: Yasujiro Kawabata, Musashino; Ikuei Ogata, Tokyo, both of Japan

[73] Assignee: Agency of Industrial Science & Technology, Tokyo, Japan

[21] Appl. No.: 124,796

[22] Filed: Feb. 26, 1980

[30] Foreign Application Priority Data

Jun. 12, 1979 [JP] Japan .................................. 54-73692

[51] Int. Cl.³ ............................................. C07C 45/50
[52] U.S. Cl. .................................................. 568/454
[58] Field of Search ....................... 568/454, 882, 909

[56] References Cited

U.S. PATENT DOCUMENTS

| | | | |
|---|---|---|---|
| 3,981,925 | 9/1976 | Schwager et al. | 568/454 |
| 3,996,293 | 12/1976 | Knifton et al. | 568/454 |
| 4,013,583 | 3/1977 | Knifton | 568/454 |
| 4,013,584 | 3/1977 | Knifton | 568/454 |
| 4,101,565 | 7/1978 | Poist | 568/454 |
| 4,198,352 | 4/1980 | Kim | 568/454 |
| 4,229,381 | 10/1980 | Ogata | 568/454 |

FOREIGN PATENT DOCUMENTS 49-20112 3/1973 Japan .................................. 568/454

*Primary Examiner*—Werren B. Lone
*Attorney, Agent, or Firm*—Armstrong, Nikaido, Marmelstein & Kubovcik

[57] ABSTRACT

In catalytic hydroformylation of an olefin with hydrogen and carbon monoxide, when a platinum-phosphine complex is used as a catalyst and a compound of tin and an element of the group VIB of the Periodic Table is used as a promotor, condensation of the formed aldehyde as a side reaction is controlled and the intended aldehyde can be obtained in a high yield.

10 Claims, 1 Drawing Figure

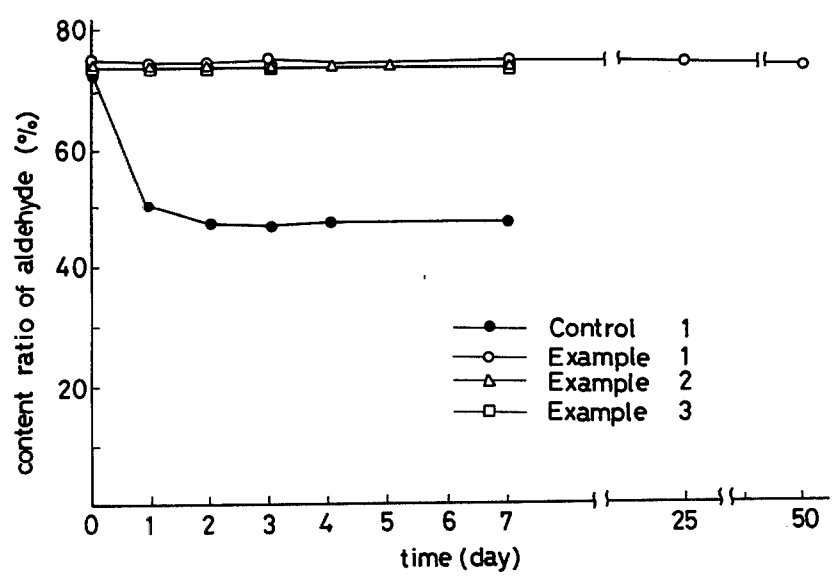

PROCESS FOR PREPARATION OF ALDEHYDES

BACKGROUND OF THE INVENTION (1) Field of the Invention

The present invention relates to a process for preparing aldehydes by hydroformylation of olefins. More particularly, the present invention relates to a process for the preparation of aldehydes by catalytic hydroformylation of olefins with hydrogen and carbon monoxide, in which the reaction is carried out in the presence of a platinum-phosphine complex and a compound of tin and an element of the group VIB of the Periodic Table and aldehydes are prepared in high yields while controlling occurrence of side reactions.

(2) Description of the Prior Art

A hydroformylation catalyst system comprising a platinum-phosphine complex and a tin halide as a promotor has been known. For example, Japanese patent application Laid-Open Specification No. 20112/74 discloses a process in which hydrogen and carbon monoxide are added to an olefin by using a platinum (II) dihalide complex having a improved ligand stabilizing effect in combination with a halide of a metal of the group IVB of the Periodic Table to form a carbonyl group-containing compound. Furthermore, Japanese patent application Laid-Open Specification No. 65810/78 discloses a process for the preparation of aldehydes which comprises reacting an olefin with carbon monoxide and hydrogen in the presence of a catalyst comprising a tetra-valent platinum compound, at least one ligand compound selected from phosphorus compounds represented by the general formula $P(R^1, R^2, R^3)$, amine compounds and tertiary arsine compounds, and a halide of a metal of the group IVB of the Periodic Table. We previously invented processes for the preparation of aldehydes by hydroformylation of olefins using platinum catalysts, in which at least one member selected from halides of metals of the group IVB of the Periodic Table is used as a promotor and a tertiary phosphine of a special steric structure capable of acting as a bidentate ligand is used as the ligand of the platinum catalyst, and filed patent applications for these inventions (see Japanese patent applications No. 26824/78 and No. 5613/79).

In each of these processes, a halide of an element of the group IVB of the Periodic Table, especially a halide of tin, is preferably used as the promotor.

However, when a halide such as stannous chloride is used as the promotor, condensation of a part of the aldehyde formed by the hydroformylation reaction is caused and the yield of the actually obtained aldehyde is drastically reduced by this reaction.

It is considered that one of the causes of this side reaction is that stannous chloride acts as a Lewis acid as is well-known in the art and aldol condensation of the formed aldehyde is caused by the catalytic action of stannous chloride. Occurrence of this side reaction is controlled by reducing the catalyst concentration to a very low level, but in this case, the reaction time is prolonged and the process is not preferred from the practical viewpoint.

We made researches with a view to developing a catalyst capable of guaranteeing a sufficient reaction speed even if the amount used of the catalyst is very small, and found the above-mentioned catalyst system including a bidentate ligand having a special structure which can highly activate a platinum catalyst. However, even if this catalyst system is employed, when the reaction is conducted for a long time, formation of an aldehyde condensate cannot be avoided.

Therefore, we furthered our researches with a view to overcoming the defects of the conventional processes for the preparation of aldehydes, and found that when a compound of tin and an element of the group VIB of the Periodic Table is used instead of a tin halide as the promotor for a platinum catalyst, an aldehyde condensate is hardly formed during or after the reaction even if the catalyst concentration is high. We have now completed the present invention based on this finding.

SUMMARY OF THE INVENTION

More specifically, in accordance with the present invention, there is provided a process for the preparation of aldehydes by hydroformylation of olefins, which comprises reacting an olefin with hydrogen and carbon monoxide in the presence of a platinum-phosphine complex catalyst, wherein the reaction is carried out in the copresence of a compound represented by the general formula $SnM_m$ wherein M stands for an element of the group VIB of the Periodic Table and m is 1 or 2, or $SnSO_4$.

BRIEF DESCRIPTION OF THE DRAWING

FIG. 1 is a graph illustrating the change, with the lapse of time, of the content of aldehyde formed by hydroformylation of an olefin.

DETAILED DESCRIPTION OF THE PREFERRED EMBODIMENTS

As the olefin that can be used in the process of the present invention, there can be mentioned, for example, alkenes such as 1-alkenes, 2-alkenes, alkadienes and derivatives thereof, alkyl alkenoates such as acrylic acid esters and methacrylic acid esters, alkenyl alkenoates such as vinyl and allyl esters of fatty acids, and alkenyl alkyl ethers such as alkyl vinyl ethers. In the present invention, the carbon number of the olefin is not particularly critical but olefins having 2 to 20 carbon atoms are preferably used.

As specific examples of such olefin, there can be mentioned ethylene, propylene, 1-butene, 1-pentene, 1-hexene, 1-heptene, 1-dodecene, 1-vinyl-2-cyclohexene, 2-methyl-1-pentene, 2-ethyl-1-hexene, styrene, methyl acrylate, methyl methacrylate, vinyl acetate and vinylmethyl ether.

In the present invention, a platinum-phosphine complex is a main catalyst. As the phosphine, 1,4-bis(diphenylphosphino)butane, trans-1,2-bis(diphenylphosphinomethyl)cyclobutane, 2,3-0-isopropylidene-2,3-dihydroxy-1,4-bis(diphenylphosphino)butane and trans-2,3-bis(diphenylphosphinomethyl)norbornane are used.

It is preferred that the platinum-phosphine complex catalyst be added to the reaction system in advance. However, the process of the present invention is not limited to this embodiment. Any of platinum compounds that can form a platinum-phosphine complex under hydroformylation conditions with a phosphine separately added can be used as a precursor. As such precursor, there can be mentioned, for example, organic platinum complex compounds and inorganic platinum salts such as $Pt(PhCN)_2Cl_2$, $K_2PtCl_4$, $Pt(1,5\text{-COD})Cl_2$ in which COD stands for cyclooctadiene and $PtCl_2$.

In the process of the present invention, a compound represented by the general formula $SnM_m$ or $SnSO_4$ is used as the promotor. As M in the formula, there can be mentioned oxygen, sulfur, selenium and tellurium, and oxygen and sulfur are especially preferred. Promotors of the above formula where m is 1 or 2 are effective, and especially good results are obtained by using a promotor in which m is 1.

As specific examples of the compound represented by the general formula $SnM_m$, there can be mentioned $SnO$, $SnO_2$, $SnS$, $SnS_2$, $SnSe$ and $SnTe$.

In practising the process of the present invention, a platinum catalyst component and a phosphine ligand or a complex catalyst formed by reaction of both the components, a tin compound represented by the formula $SnM_m$ as a promotor or $SnSO_4$, and an olefin are charged in a pressure vessel, and the olefin is reacted with a mixed gas of carbon monoxide and hydrogen (synthesis gas) fed under pressure. The reaction may be advanced even if a solvent is not added. However, when an ordinary solvent is made present in the reaction system, good results are obtained with respect to the uniformalization and stabilization of the catalyst system. As the solvent that can be used in the process of the present invention, there can be mentioned, for example, aliphatic saturated hydrocarbons such as hexane and heptane, alicyclic hydrocarbons such as cyclohexane and decalin, aromatic hydrocarbons such as benzene, toluene and tetralin, ethers such as diethyl ether and tetrahydrofuran, halogenated hydrocarbons such as methylene chloride and chlorobenzene, ketones such as acetone and methylethyl ketone and alcohols such as methanol and ethanol. It is especially preferred that a solvent having a high boiling point be used so that the catalyst is left in the solution even after recovery of the reaction product by distillation, because recovery and re-use of the catalyst can be performed conveniently and industrial advantages are attained. The amount used of the solvent is not particularly critical, but if the amount of the solvent is too large, the reaction speed is reduced. Accordingly, it is ordinarily preferred that the solvent be used in an amount of less than 10 parts by volume per part by volume of the liquid olefin.

The amount of the platinum catalyst used in the form of a complex with the phosphine may be small in the present invention. The amount of the platinum catalyst is ordinarily determined according to the reaction conditions, the kind of the olefin as the basic reactant and the desired reaction speed. Ordinarily, the platinum catalyst is used in an amount of $1.0 \times 10^{-5}$ to $1.0 \times 10^{-3}$ mole, calculated as the platinum atom, per mole of the olefin.

The amount of the phosphine to be used as the ligand to platinum is determined according to the coordination activity and the reaction conditions. Ordinarily, the amount of the ligand is less than 10 moles per platinum atom, and it is preferred that the ligand be used in an amount of 0.5 to 5 moles per platinum atom.

The amount of a tin compound represented by the general formula $SnM_m$ or $SnSO_4$ that is used as the promotor in the process of the present invention is less than 50 atoms as tin, preferably 0.5 to 20 atoms as tin, per platinum atom.

In the process of the present invention, the reaction is carried out by controlling the mixing molar ratio of carbon monoxide and hydrogen within a range of from 1:10 to 10:1, and it is preferred that this ratio be adjusted within a range of from 1:2 to 30:1. In this reaction, each of carbon monoxide and hydrogen is consumed in an amount of 1 mole per mole of the olefin. The total pressure of the mixed gas of carbon monoxide and hydrogen is selected within a range of from 5 to 500 Barr., preferably 50 to 200 Barr. The lower is the reaction temperature, the higher is the selectivity to the aldehyde. In view of the relation between the selectivity to the aldehyde and the reaction speed, it is ordinarily preferred that the reaction temperature be 40 to 200° C., especially 50 to 150° C.

According to the process of the present invention, in hydroformylation of an olefin, formation of an aldehyde condensate can be remarkably reduced, and the corresponding aldehyde can be obtained in a very high yield. Furthermore, in the process of the present invention, separation and recovery of the catalyst from the reaction product can be remarkably facilitated and the efficiency of re-use of the catalyst can be highly improved.

Moreover, according to the process of the present invention, there can be attained an advantage that formation of a condensate of the formed aldehyde is prevented even after completion of the hydroformylation reaction.

The present invention will now be described in detail with reference to the following Examples that by no means limit the scope of the present invention.

EXAMPLES 1 through 4

In a reaction vessel having an inner capacity of 50 ml were charged 15.1 mg ($3.2 \times 10^{-5}$ mole) of $Pt(PhCN)_2Cl_2$, $3.2 \times 10^{-5}$ mole of 2,3-0-isopropylidene-2,3-dihydroxy-1,4-bis(diphenylphosphino)butane and 21.6 mg ($21.6 \times 10^{-4}$ mole) of SnO (Example 1), 24.1 mg ($1.6 \times 10^{-4}$ mole) of SnS (Example 2), 24.1 mg ($1.6 \times 10^{-4}$ mole) of $SnO_2$ (Example 3) or 34.3 mg ($1.6 \times 10^{-4}$ mole) of $SnSO_4$ (Example 4), and the inside atmosphere of the reaction vessel was replaced by nitrogen. Then, 18 ml of benzene as a solvent was added to the charge of the reaction vessel and 3 ml ($2.7 \times 10^{-2}$ mole) of 1-pentene was added, and a mixed gas of carbon monoxide and hydrogen (mixing volume ratio = 1:1) was fed under 100 atmospheres at room temperature.

Then, the reaction vessel was immersed in an oil bath maintained at 100° C. and agitation was initiated. When this state was maintained for 1 hour, reduction of the pressure in the reaction vessel was stopped. The reaction speed was obtained as a function of the time by plotting the pressure in the reaction vessel. At the point when the reaction was completed, the reaction vessel was cooled and the reaction product was analyzed to obtain results shown in Table 1.

Each of the reaction product mixture liquids obtained in Examples 1 through 4 was allowed to stand still at room temperature and the change of the aldehyde content with the lapse of time was measured to obtain results shown in graphs of FIG. 1.

CONTROL 1

The reaction was carried out in the same manner as in Examples 1 to 3 except that $1.6 \times 10^{-4}$ mole of $SnCl_2.2H_2O$ was used instead of SnO, SnS or $SnO_2$. The product was analyzed by gas chromatography to obtain results shown in Table 1. The resulting reaction mixture liquid was allowed to stand still at room temperature and the change of the aldehyde content with the lapse of time was measured to obtain results shown in a graph of Control 1 in FIG. 1.

TABLE 1

|  | Example 1 | Example 2 | Example 3 | Example 4 | Control 1 |
|---|---|---|---|---|---|
| Promotor[1] | SnO | SnS | $SnO_2$ | $SnSO_4$ | $SnCl_2 \cdot 2H_2O$ |
| Reaction Time(hours) | 3.5 | 3.0 | 7.0 | 4.0 | 1.0 |
| Conversion (%) | 100 | 100 | 100 | 100 | 100 |
| Reaction Speed[2] | 22 | 30 | 11 | 17 | 100 |
| Composition (%) of Product |  |  |  |  |  |
| aldehyde | 75.8 | 75.4 | 73.7 | 74.2 | 72.3 |
| n-aldehyde/iso-aldehyde ratio | 95/5 | 95/5 | 95/5 | 95/5 | 95/5 |
| aldehyde condensate | 0.2 | 0.1 | 0.1 | ~0 | 2.5 |
| hydrogenation product (n-pentane) | 9.2 | 9.1 | 9.2 | 9.8 | 9.9 |
| isomerization product (2-pentene) | 14.8 | 15.5 | 17.0 | 16.0 | 15.3 |

Note
[1] The amount used of the promotor was $1.6 \times 10^{-4}$ mole.
[2] The reaction speed is expressed in terms of a relative value calculated based on the presumption that the gradient of the curve obtained by plotting the relation between the reaction time and the pressure reduction in Control 1 is 100.

As will be apparent from the results shown in Table 1, in Control 1 using $SnCl_2$ as a promotor, the amount of the aldehyde was 72.3% as analyzed just after completion of the reaction and in addition, the aldehyde condensate was formed in an amount of 2.5%. If this reaction mixture liquid formed in Control 1 was allowed to stand still at room temperature, about 30% of the formed aldehyde was converted to a condensate within 1 to 3 days. Ordinarily, the aldehyde formed by hydroformylation is industrially separated and purified by heating and distillation under reduced pressure and the catalyst is recovered from the distillation residue and used again. Accordingly, when the yield of the aldehyde is low and a high-boiling-point aldehyde condensate formed in a large quantity by the side reaction is present together with the catalyst as in case of Control 1, the recovery of the catalyst is very difficult.

In contrast, in Examples 1 through 4 of the present invention, the amounts of the aldehyde as analyzed just after completion of the reaction were larger and 75.8%, 75.4%, 73.7% and 74.2%, respectively, though the reaction speed was lower than in Control 1. Furthermore, in Examples 1 through 4, the amounts of the aldehyde condensate were very small and 0.2%, 0.1%, 0.1% and substantially 0%, respectively. Furthermore, from the results shown in FIG. 1, it will readily be understood that even if the reaction mixture liquid formed according to the process of the present invention is allowed to stand still, an aldehyde condensate is hardly formed.

CONTROL 2

The reaction was carried out in the same manner as described in Control 1 except that 4 ml ($3.2 \times 10^{-2}$ mole) of 2-methylpentene-1 was used as the olefin instead of 1-pentene and 16 ml of benzene was used as the solvent. The reaction was completed in 3 hours. The as-prepared reaction mixture liquid was analyzed by gas chromatography, and the reaction mixture liquid was allowed to stand still at room temperature for 7 days and was analyzed by gas chromatography. The obtained results are shown in Table 2.

EXAMPLE 5

The hydroformylation reaction was carried out in the same manner as described in Control 2 except that SnO was used instead of $SnCl_2 \cdot 2H_2O$, to obtain results shown in Table 2.

From the results shown in Table 2, it will readily be understood that in the process of the present invention, formation of an aldehyde condensate is remarkably reduced.

TABLE 2

|  | Example 5 | Control 2 |
|---|---|---|
| Promotor | SnO | $SnCl_2 \cdot 2H_2O$ |
| Reaction Time (hours) | 5 | 3 |
| Reaction Speed[1] | 13 | 18 |
| Conversion (%) | 91.3 | 98.8 |
| Composition (%) of product |  |  |
| aldehyde |  |  |
| just after reaction | 85.3 | 82.4 |
| after 7 days' standing | 84.4 | 67.7 |
| aldehyde condensate |  |  |
| just after reaction | 0.1 | 7.5 |
| after 7 days' standing | 1.2 | 22.5 |
| unreacted 2-methylpentene-1 |  |  |
| just after reaction | 8.7 | 1.2 |
| after 7 days' standing | 8.7 | 1.2 |
| hydrogenation product (2-methylpentene) |  |  |
| just after reaction | 3.9 | 2.7 |
| after 7 days' standing | 3.8 | 2.6 |
| isomerization product (2-methylpentene-2) |  |  |
| just after reaction | 2.0 | 6.2 |
| after 7 days' standing | 1.9 | 6.3 |

Note
[1] The reaction speed is expressed in terms of a relative value calculated based on the presumption that the gradient of the curve obtained by plotting the relation between the reaction time and the pressure reduction in Control 1 is 100.

EXAMPLES 6 and 7

The reaction was carried out in the same manner at the same mixture ratio under the same conditions as in Examples 1 to 3 except that 1-pentene was used as the olefin, trans-2,3-bis(diphenylphosphinomethyl)norbornane was used as the phosphine and SnO was used as the promotor. The obtained results are shown in Table 3 (Example 6).

The solvent and formed aldehyde were removed from the reaction product mixture formed in Example 6 by distillation in a nitrogen atmosphere, and the same amounts of 1-pentene and benzene as in Example 6 were added to the residual catalyst, and the reaction was carried out under the same conditions as in Example 6. The obtained results are shown in Table 3 (Example 7).

TABLE 3

|  | Example 6 | Example 7 |
|---|---|---|
| Reaction Time (hours) | 4 | 4 |
| Reaction Speed[1] | 12 | 14 |
| Conversion (%) | 100 | 100 |
| Composition (%) of Product |  |  |
| aldehyde | 75.2 | 72.8 |
| n-aldehyde/iso-aldehyde ratio | 98/2 | 98/2 |
| aldehyde condensate | ~0 | ~0 |
| hydrogenation product (n-pentene) | 7.3 | 8.5 |
| isomerization product (2-pentene) | 17.5 | 18.7 |

Note
[1] The reaction speed is expressed in terms of a relative value calculated based on the presumption that the gradient of the curve obtained by plotting the relation between the reaction time and the pressure reduction in Control 1 is 100.

From the results shown in Table 3, it will readily be understood that according to the process of the present invention, the catalyst can be used repeatedly and no substantial formation of the aldehyde condensate is observed.

What we claim is:

1. A process for the preparation of aldehydes by hydroformylation of olefins, which comprises reacting an olefin with hydrogen and carbon monoxide in the presence of a platinum-phosphine complex catalyst, wherein a compound represented by the following general formula:

$$SnM_m$$

wherein M stands for an element of the group VIB of the Periodic Table and m is 1 or 2, or
$SnSO_4$ is used as a promotor for said reaction wherein an aldehyde is formed by hydroformylation of said olefin.

2. A process according to claim 1 wherein M is oxygen or sulfur.

3. A process according to claim 2 wherein m is 1.

4. A process according to claim 1 wherein the platinum-phosphine complex catalyst consists of platinum and a tertiary phosphine capable of acting as a bidentate ligand.

5. A process according to claim 1 wherein the platinum-phosphine complex catalyst is formed from a platinum compound and a tertiary phosphine in the reaction system of said hydroformylation of olefins.

6. A process according to claim 1 wherein the hydroformylation reaction is carried out at a temperature of from 40° to 200° C.

7. A process according to claim 1 wherein the hydroformylation reaction is carried out under a pressure of from 5 to 500 Barr.

8. A process according to claim 1 wherein the platinum-phosphine complex catalyst is used in an amount of from $10^{-5}$ to $10^{-3}$ mole as calculated as the platinum atom per mole of the olefin.

9. A process according to claim 1 wherein the promotor is used in an amount of from 0.5 to 20 atoms as calculated as the tin per atom of platinum.

10. A process according to claim 1 wherein hydrogen and carbon monoxide are used at a molar ratio of from 1:10 to 10:1.

* * * * *